(12) United States Patent
Chen et al.

(10) Patent No.: US 11,530,212 B2
(45) Date of Patent: Dec. 20, 2022

(54) FLUORESCENT PROBE COMPOUND FOR ZINC ION, AS WELL AS PREPARATION METHOD AND USE THEREOF

(71) Applicant: Wuyi University, Jiangmen (CN)

(72) Inventors: Xiuwen Chen, Jiangmen (CN); Ziyin Guo, Jiangmen (CN); Ziping Zhang, Jiangmen (CN); Xuyan Chen, Jiangmen (CN); Zhongzhi Zhu, Jiangmen (CN); Zhihai Yang, Jiangmen (CN)

(73) Assignee: WUYI UNIVERSITY, Jiangmen (CN)

( * ) Notice: Subject to any disclaimer, the term of this patent is extended or adjusted under 35 U.S.C. 154(b) by 241 days.

(21) Appl. No.: 16/964,853

(22) PCT Filed: May 9, 2020

(86) PCT No.: PCT/CN2020/089423
§ 371 (c)(1),
(2) Date: Jul. 24, 2020

(87) PCT Pub. No.: WO2020/228640
PCT Pub. Date: Nov. 19, 2020

(65) Prior Publication Data
US 2021/0147412 A1    May 20, 2021

(30) Foreign Application Priority Data
May 13, 2019   (CN) .......................... 2019103931756

(51) Int. Cl.
*C07D 471/00* (2006.01)
*C07D 471/04* (2006.01)
(Continued)

(52) U.S. Cl.
CPC ............ *C07D 471/04* (2013.01); *C09K 11/07* (2013.01); *G01N 21/643* (2013.01);
(Continued)

(58) Field of Classification Search
CPC .................................................... C07D 471/04
(Continued)

(56) References Cited

U.S. PATENT DOCUMENTS

2005/0250214 A1   11/2005   Gee
2007/0179311 A1 *  8/2007   Banerjee ................. A61P 39/04
                                                            562/400

FOREIGN PATENT DOCUMENTS

CN        101446547 A     6/2009
CN        102925136 A     2/2013
(Continued)

OTHER PUBLICATIONS

International Searching Authority. International Search Report and Written Opinion for PCT Application No. PCT/CN2020/089423 and English translation, dated Aug. 6, 2020, pp. 1-13.
(Continued)

*Primary Examiner* — Christine T Mui
*Assistant Examiner* — Emily R. Berkeley
(74) *Attorney, Agent, or Firm* — Vivacqua Crane, PLLC

(57) ABSTRACT

The present disclosure relates to the field of organic light emitting materials, and in particular, to a fluorescent probe compound for zinc ion, as well as a preparation method and use in zinc ion detection thereof. The fluorescent probe compound of the present disclosure has a name of 2-(7-(2, 8-dimethyl quinoline-6-yl)-5,6,7,8-tetrahydro-1,8-naphthyridin-2-yl) phenol, and is synthesized with 2,8-dimethyl tetrahydroquinoline and 2-(2-phenolyl)-1,8-naphthyridine as main raw materials. Fluorescence property tests show that the fluorescent probe compound of the present disclosure has a high selectivity and sensitivity for $Zn^{2+}$, a high chemical stability and a good water solubility, which particularly suitable for detecting $Zn^{2+}$ in a water environment system. The excitation and emission spectrums of the com-
(Continued)

pound are in a visible region, which could serve as a fluorescent probe applied to the field of zinc ion detection.

10 Claims, 6 Drawing Sheets

(51) Int. Cl.
 *C09K 11/07* (2006.01)
 *G01N 21/64* (2006.01)
 *G01N 33/18* (2006.01)

(52) U.S. Cl.
 CPC .. *G01N 33/1813* (2013.01); *C09K 2211/1007* (2013.01); *C09K 2211/1029* (2013.01); *C09K 2211/188* (2013.01); *G01N 2021/6439* (2013.01)

(58) Field of Classification Search
 USPC .......................................................... 436/81
 See application file for complete search history.

(56) References Cited

FOREIGN PATENT DOCUMENTS

| | | |
|---|---|---|
| CN | 105038769 A | 11/2015 |
| CN | 107118206 A | 9/2017 |
| CN | 107523292 A | 12/2017 |
| CN | 107628997 A | 1/2018 |
| CN | 108250211 A | 7/2018 |
| CN | 109053725 A | 12/2018 |
| CN | 109180705 A | 1/2019 |
| CN | 109293651 A | 2/2019 |
| CN | 110117282 A | 8/2019 |
| CN | 108299402 B | 3/2021 |
| JP | 2005325074 A | 11/2005 |

OTHER PUBLICATIONS

The State Intellectual Property Office of People's Republic of China. First Office Action for CN Application No. 2019103931756 and English translation, dated Jan. 10, 2020, pp. 1-8.

The State Intellectual Property Office of People's Republic of China First Search Report for CN Application No. 2019103931756 and English translation, dated Jan. 2, 2020, pp. 1-6.

* cited by examiner

FLUORESCENT PROBE COMPOUND FOR ZINC ION, AS WELL AS PREPARATION METHOD AND USE THEREOF

CROSS REFERENCE TO RELATED APPLICATIONS

The present application is a national phase entry under 35 USC § 371 of International Application PCT/CN 2020/089423, filed on 9 May 2020, which claims the benefit of and priority to Chinese Patent Application No. 2019103931756, filed on 13 May 2019, the entire disclosures of which are incorporated herein by reference.

TECHNICAL FIELD

The present disclosure relates to the field of organic light-emitting materials, and in particular, to a fluorescent probe compound for zinc ion, its preparation method and use in zinc ion detection.

BACKGROUND

Zinc ion is one of essential trace elements in organism, which has important physiological functions and is a component of various proteins and enzymes in human body. The zinc ion is widely involved in physiological activities. A too large or too small content of zinc ions will lead to dysfunction of the organism. High-sensitive detection of zinc ion has a reference value for disease diagnosis. Therefore, selective recognition and detection of zinc ion are of very great importance to the related research in the fields of chemistry, biology, clinical medicine and the like. Molecular probe can detect information such as concentration, distribution and the like of target object in real time, and thus has the potential for real-time analysis and detection of zinc ions in organism.

Fluorescent probe has advantages of low cost, simple operation, low detection limit, good selectivity, real-time monitoring, etc., and has attracted extensive attention in metal ion detection. Because fluorescence-enhanced sensing material could reduce detection errors, accurately detect a complex system and detect different analytes simultaneously with multiple detectors. However, the currently reported fluorescent chemical probes for Zn2+ are still subjected to certain limitations in practical application, for example, some are lack of specificity and easily been interfered by other metal ions; some are difficult to synthesize and complicated in structure; some have poor membrane permeability; some need an organic solvent to facilitate dissolution during the process of zinc ion detection, which increases the toxicity of the detection system and limits the use of the fluorescent probes in a biological system. Therefore, there has been a lack of a fluorescent probe compound with high sensitivity, good selectivity, and excellent propertys while capable of realizing aqueous phase detection of $Zn^{2+}$.

SUMMARY

In view of the defects existing in the above prior arts, the present disclosure aims at providing a fluorescent probe compound for zinc ion, as well as preparation method and use thereof. The fluorescent probe compound of the present disclosure has a high selectivity and sensitivity for $Zn^{2+}$, and could be used in the field of zinc ion detection as a fluorescent probe thus.

The present disclosure adopts the following technical scheme:

A fluorescent probe compound has a name of 2-(7-(2,8-dim ethyl quinoline-6-yl)-5,6,7,8-tetrahydro-1,8-naphthyridin-2-yl) phenol. The structural formula is as follows:

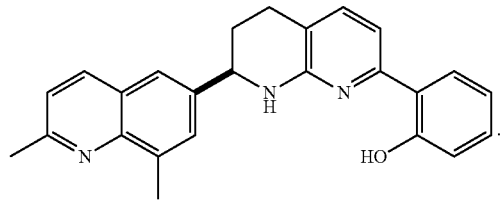

A preparation method of the aforesaid fluorescent probe compound, including the following steps:

uniformly mixing 2,8-dimethyl tetrahydroquinoline, 2-(2-phenolyl)-1,8-naphthyridine, metal catalyst, acid and solvent, reacting at 80-160° C. for 5-24 hours to obtain a crude product; and purifying the crude product to obtain the fluorescent probe compound.

The reaction equation and principle involved in the aforesaid preparation method are as follows:

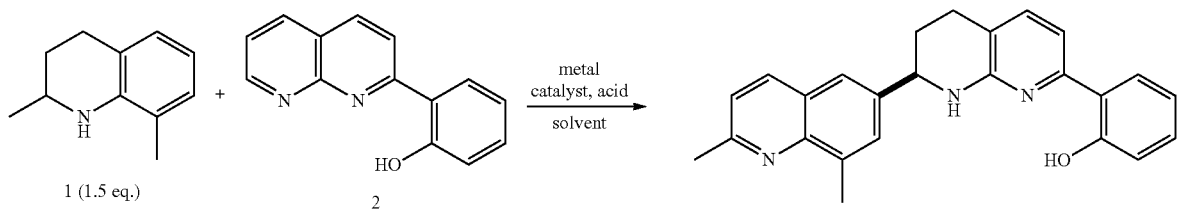

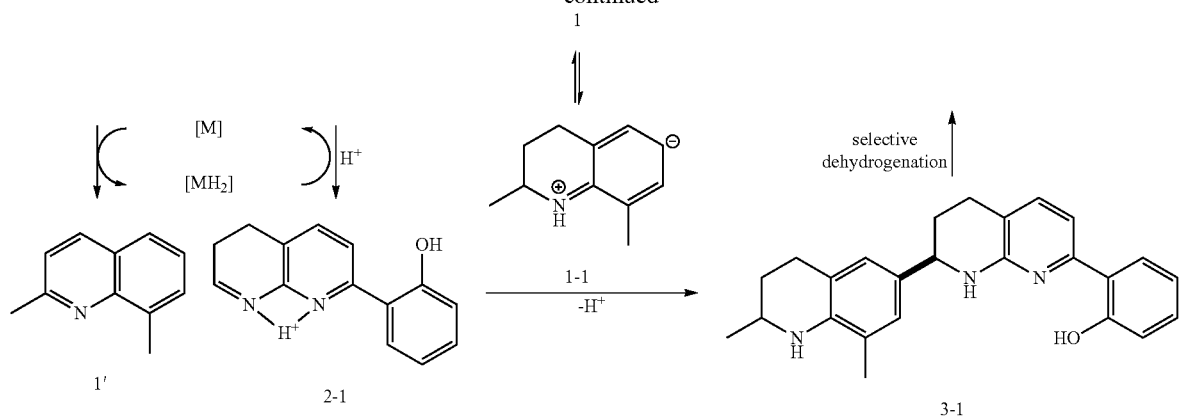

In the present disclosure, under the catalysis of the metal catalyst (M), 0.5 equivalents of 2,8-dimethyl tetrahydroquinoline (compound 1, with total amount of 1.5 equivalents) is completely dehydrogenated to generate a compound 1' and [MH2]. Meanwhile, compound 2-1 is generated from 2-(2-phenolyl)-1,8-naphthyridine (compound 2) under the action of [MH2], and then, under the action of an acid, 1 equivalent of the compound 1 generates compound 1-1. Like a Friedel-Crafts reaction, compound 3-1 is obtained through conjugate addition between the electron-rich compound 1-1 and the compound 2-1, and then the compound 3-1 converts to compound 3 through tautomerism.

Preferably, the reaction is carried out with exclusion of the air.

Further preferably, exclusion of the air is under an atmosphere of nitrogen.

Preferably, the molar ratio of the 2,8-dimethyl tetrahydroquinoline to the 2-(2-phenolyl)-1,8-naphthyridine is 1:0.5-1.

Preferably, the metal catalyst is selected from one or more of: copper acetate, copper trifluoromethylsulfonate, copper sulfate, copper chloride, cuprous chloride, ferric chloride, cobalt acetate, cobalt chloride and manganese acetate; and the mass of the metal catalyst is 1-5% of the mass of the 2,8-dimethyl tetrahydroquinoline.

In the present disclosure, catalysis could be effectively realized with an inexpensive metal catalyst, thereby greatly reducing the production cost.

Preferably, the acid is selected from one or more of: formic acid, acetic acid, methylsulfonic acid, benzoic acid, p-toluenesulfonic acid, hydrochloric acid, trifluoromethylsulfonic acid, and trifluoroacetic acid; and the mass of the acid is 10-100% of the mass of the 2,8-dimethyl tetrahydroquinoline.

Preferably, the solvent is selected from one or more of: ethanol, tert-pentanol, isopropanol, 1,4-dioxane, N,N-dimethylformamide, dimethyl sulfoxide, toluene, p-xylene and water.

Preferably, the volume molar ratio of the solvent to the 2,8-dimethyl tetrahydroquinoline is 0.5-3 mL:0.5 mmol.

Preferably, the purification is column chromatography purification.

Further preferably, the eluent of the column chromatography purification is a mixed solution of petroleum ether: dichloromethane:ethyl acetate in a volume ratio of 0.5-50: 0-20:1.

The use of the aforesaid fluorescent probe compound in zinc ion detection, including the uses in a fluorescent probe, a high-sensitive sensor or a zinc-ion detection instrument.

The present disclosure has the following prominent technical effects: (1) In the present disclosure, the fluorescent probe compound is synthesized by using 2,8-dimethyl tetrahydroquinoline and 2-(2-phenolyl)-1,8-naphthyridine as main raw materials, which has simple synthesis steps, a safe operating method, nonpoisonous raw materials and a low price.

(2) The excitation and emission spectrums of the fluorescent probe compound in the present disclosure are in a visible light region, the fluorescent probe compound has a high selectivity and sensitivity for $Zn^{2+}$, a high chemical stability and a good water solubility, which could detect $Zn^{2+}$ in a water environment system, and thus can be effectively applied to a fluorescent probe, a high-sensitive sensor or a zinc-ion detection instrument.

DETAILED DESCRIPTION

The present disclosure is described in detail in connection with the following examples:

Example 1

A preparation method of a fluorescent probe compound, including the following steps:

uniformly mixing 0.161 g of 2,8-dimethyl tetrahydroquinoline (1 mmol), 0.111 g of 2-(2-phenolyl)-1,8-naphthyridine (0.5 mmol), 0.0016 g of copper trifluoromethylsulfonate (1% of the mass of 2,8-dimethyl tetrahydroquinoline), 0.08 g of trifluoromethylsulfonic acid (50% of the mass of 2,8-dimethyl tetrahydroquinoline) and 1.5 mL of toluene, reacting with stirring at 80° C. under an atmosphere of nitrogen for 24 hours to obtain a crude product; and purifying the crude product by column chromatography to obtain a fluorescent probe compound. The yield of this preparation method was 78%, and the fluorescent probe compound was presented as a yellow solid.

Figure 1:
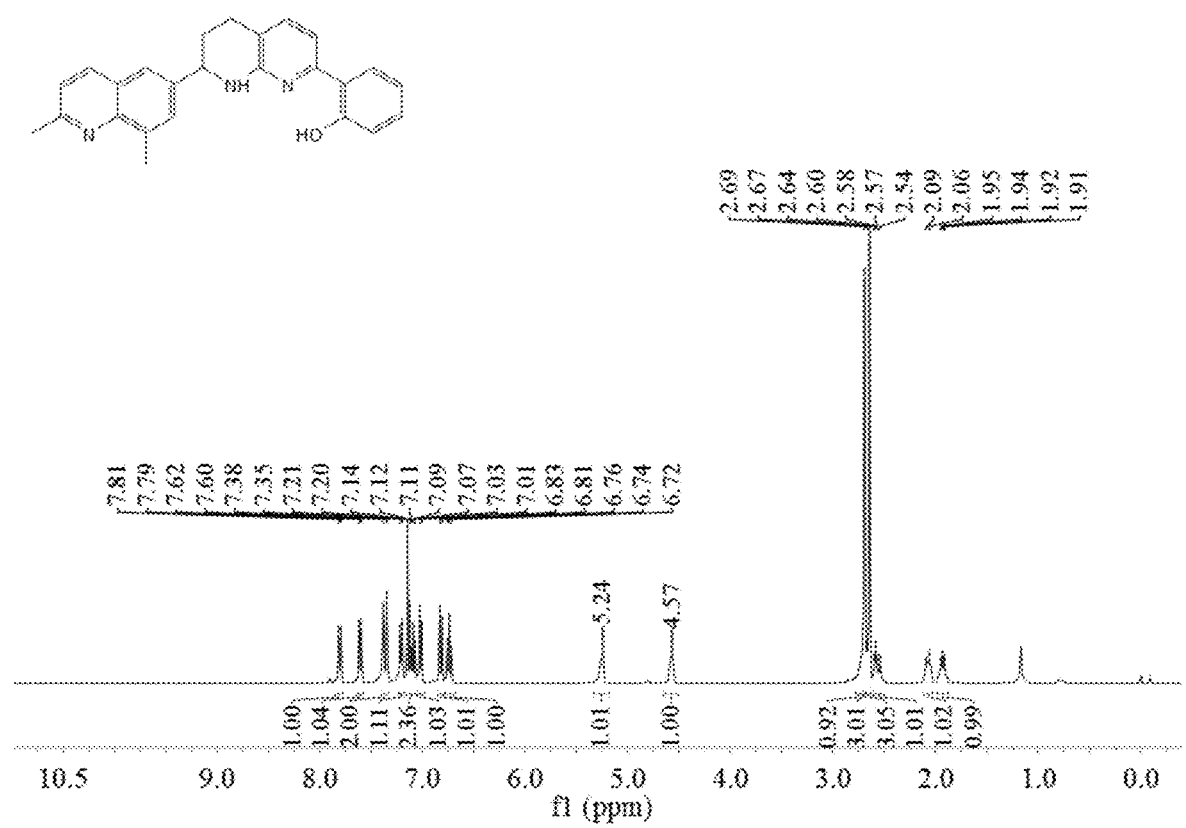
FIG. 1 is a nuclear magnetic resonance hydrogen spectrum of the fluorescent probe compound of the present disclosure.
Figure 2:
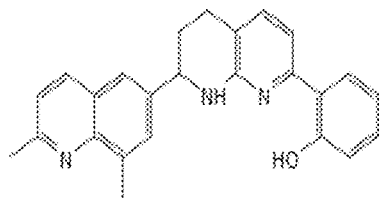
FIG. 2 is a nuclear magnetic resonance carbon spectrum of the fluorescent probe compound of the present disclosure.
Figure 2:
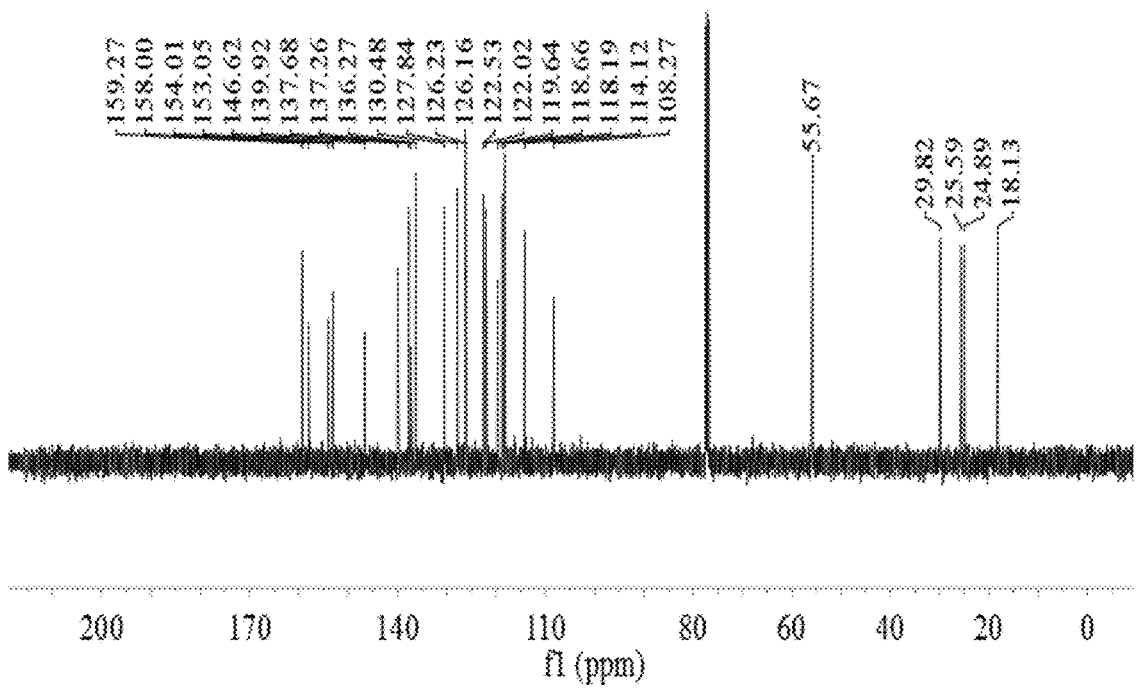

The nuclear magnetic resonance hydrogen spectrum and nuclear magnetic resonance carbon spectrum of the resultant fluorescent probe compound were shown in FIGS. 1 and 2, and the structural characterization data was as follows:

nuclear magnetic resonance hydrogen spectrum data: 1H NMR (400 MHz, CDCl3) δ 7.80 (d, J=8.3 Hz, 1H), 7.61 (d, J=8.0 Hz, 1H), 7.36 (d, J=13.1 Hz, 2H), 7.21 (d, J=7.7 Hz, 1H), 7.16-7.06 (m, 2H), 7.02 (d, J=7.8 Hz, 1H), 6.82 (d, J=8.1 Hz, 1H), 6.74 (t, J=7.5 Hz, 1H), 5.24 (s, 1H), 4.57 (s, 1H), 2.80-2.69 (m, 4H), 2.69 (s, 3H), 2.64 (s, 3H), 2.60-2.50 (m, 1H), 2.12-2.03 (m, 1H), 1.99-1.87 (m, 1H).

carbon spectrum data: 13C NMR (101 MHz, CDCl3) δ 159.27, 158.00, 154.01, 153.05, 146.62, 139.92, 137.68, 137.26, 136.27, 130.48, 127.84, 126.23, 126.16, 122.53, 122.02, 119.64, 118.66, 118.19, 114.12, 108.27, 55.67, 29.82, 25.59, 24.89, 18.13.

High resolution mass spectrometry (electrospray ionization mass spectrometry): theoretical calculation for C25H24N3O [M+H]+: 382.1914; found: 382.1917.

According to the aforesaid data, it was presumed that the resultant fluorescent probe compound was 2-(7-(2,8-dimethylquinoline-6-yl)-5,6,7,8-tetrahydro-1,8-naphthyridin-2-yl)phenol, which had the following structural formula:

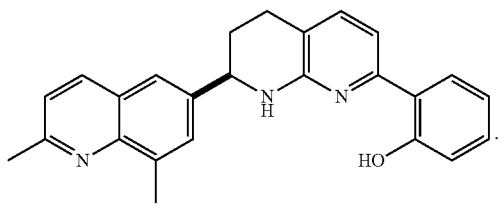

Example 2

A preparation method of a fluorescent probe compound, including the following steps:

uniformly mixing 0.121 g of 2,8-dimethyl tetrahydroquinoline (0.75 mmol), 0.111 g of 2-(2-phenolyl)-1,8-naphthyridine (0.5 mmol), 0.002 g of cobalt acetate (2% of the mass of 2,8-dimethyl tetrahydroquinoline), 0.012 g of p-toluenesulfonic acid (10% of the mass of 2,8-dimethyl tetrahydroquinoline) and 1.2 mL of toluene, reacting with stirring at 130° C. under an atmosphere of nitrogen for 15 hours to obtain a crude product; and purifying the crude product by column chromatography to obtain a fluorescent probe compound. The yield of the preparation method was 69%, and the characterization result of the fluorescent probe compound was the same as that of Example 1.

Example 3

A preparation method of a fluorescent probe compound, including the following steps:

uniformly mixing 0.129 g of 2,8-dimethyl tetrahydroquinoline (0.8 mmol), 0.089 g of 2-(2-phenolyl)-1,8-naphthyridine (0.4 mmol), 0.006 g of copper acetate (5% of the mass of 2,8-dimethyl tetrahydroquinoline), 0.065 g of trifluoroacetic acid (50% of the mass of 2,8-dimethyl tetrahydroquinoline) and 1.2 mL of tert-pentanol, reacting with stirring at 100° C. under an atmosphere of nitrogen for 10 hours to obtain a crude product; and purifying the crude product by column chromatography to obtain a fluorescent probe compound. The yield of this preparation method was 76%, and the characterization result of the fluorescent probe compound was the same as that of Example 1.

Example 4

A preparation method, of a fluorescent probe compound, including the following steps:

uniformly mixing 0.064 g of 2,8-dimethyl tetrahydroquinoline (0.4 mmol), 0.089 g of 2-(2-phenolyl)-1,8-naphthyridine (0.4 mmol), 0.002 g of copper chloride (3% of the mass of 2,8-dimethyl tetrahydroquinoline), 0.064 g of p-toluenesulfonic acid (100% of the mass of 2,8-dimethyl tetrahydroquinoline) and 1.2 mL of p-xylene, reacting with stirring at 150° C. under an atmosphere of nitrogen for 10 hours to obtain a crude product; and purifying the crude product by column chromatography to obtain a fluorescent probe compound. The yield of this preparation method was 81%, and the characterization result of the fluorescent probe compound was the same as that of Example 1.

Example 5

A preparation method of a fluorescent probe compound, including the following steps:

uniformly mixing 0.129 g of 2,8-dimethyl tetrahydroquinoline (0.8 mmol), 0.111 g of 2-(2-phenolyl)-1,8-naphthyridine (0.5 mmol), 0.006 g of ferric chloride (5% of the mass of 2,8-dim ethyl tetrahydroquinoline), 0.077 g of methylsulfonic acid (60% of the mass of 2,8-dimethyl tetrahydroquinoline) and 1 mL of toluene, reacting with stirring at 160° C. under an atmosphere of nitrogen for 12 hours to obtain a crude product; and purifying the crude product by column chromatography to obtain a fluorescent probe compound. The yield of the preparation method was 77%, and the characterization result of the fluorescent probe compound was the same as that of Example 1.

Example 6

A preparation method of a fluorescent probe compound, including the following steps:

uniformly mixing 0.161 g of 2,8-dimethyl tetrahydroquinoline (1 mmol), 0.111 g of 2-(2-phenolyl)-1,8-naphthyridine (0.5 mmol), 0.008 g of manganese acetate (5% of the mass of 2,8-dimethyl tetrahydroquinoline), 0.097 g of trifluoromethylsulfonic acid (60% of the mass of 2,8-dimethyl tetrahydroquinoline) and 1 mL of p-xylene, reacting with stirring at 160° C. under an atmosphere of nitrogen for 5 hours to obtain a crude product; and purifying the crude product by column chromatography to obtain a fluorescent probe compound; The yield of the preparation method was 64%, and the characterization result of the fluorescent probe compound was the same as that of Example 1.

Experimental Embodiment

The fluorescence property of the fluorescent probe compound according to the present disclosure was measured, including the following steps:

(1) Formulating a Probe Solution:

formulating a solution of 2-(7-(2,8-dimethyl quinoline-6-yl)-5,6,7,8-tetrahydro-1,8-naphthyridin-2-yl) phenol with a concentration of 100 μM in methanol, i.e. a probe solution, and stored at room temperature.

(2) Formulating Metal Ion Solutions:

the metal ions including: $Mg^{2+}$, $Fe^{2+}$, $Cu^+$, $Cu^{2+}$, $Sn^{4+}$, $Co^{2+}$, $Mn^{2+}$, $K^+$, $Li^+$, $Ba^{2+}$, $Ca^{2+}$, $Cd^{2+}$, $Ni^{2+}$, $Fe^{3+}$, $Al^{3+}$ and $Zn^{2+}$; and the respectively solutions of them were prepared from the corresponding hydrochloride salts thereof. Taking a certain amount of metal salts, dissolved in 10 mL of distilled water to formulate a 10-2 mol/L metal ion solution, and stored for later use.

Figure 3:
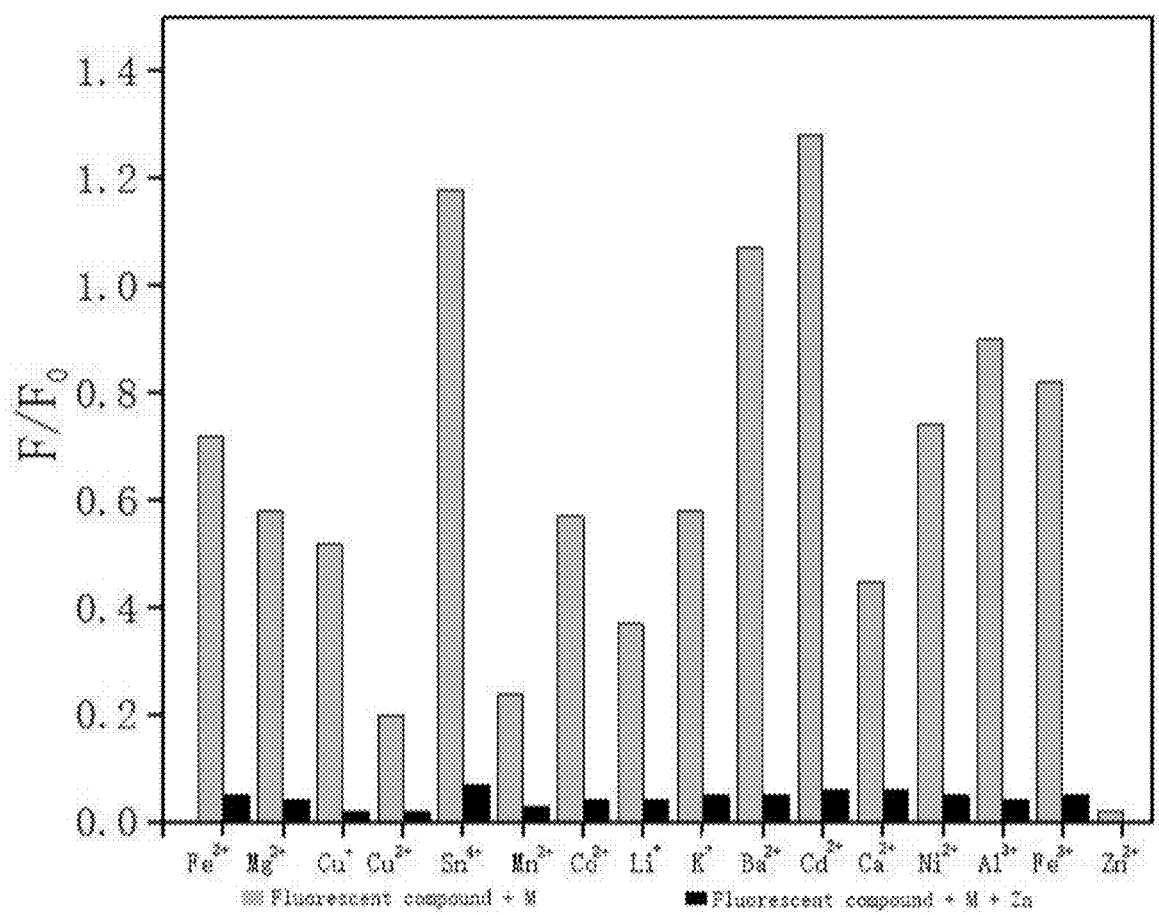
FIG. 3 is a graph of fluorescence performance test results of the fluorescent probe compound of the present disclosure under the condition of different metal ions.

(3) Fluorescence Property Test:

Experimental Embodiment 1 formulating solution to be tested: taking 0.5 mL of the formulated probe solution and 0.5 mL of the formulated metal ion solution, mixing with 4 mL solution of a $CH_3OH$—$H_2O$ (v:v=1:1) to obtain a solution to be tested of the metal ion.

formulating blank solution: taking 0.5 mL of the formulated probe solution, mixed with solution of 2.5 mL water and 2 mL methanol.

analyzing the fluorescence intensity of solution to be tested by fluorescence spectrum, and the analysis result was shown in FIG. 3.

It can be seen from FIG. 3, in the solution to be tested, when the metal ions were $Mg^{2+}$, $Fe^{2+}$, $Cu^+$, $Cu^{2+}$, $Sn^{4+}$, $Co^{2+}$, $Mn^{2+}$, $K^+$, $Li^+$, $Ba^{2+}$, $Ca^{2+}$, $Cd^{2+}$, $Ni^{2+}$, $Fe^{3+}$ or $Al^{3+}$, the fluorescence intensity of the solution to be tested changed slightly. Only the fluorescence intensity of the $Zn^{2+}$ solution to be tested showed a significant fluorescence decay (all solutions to be tested were uniformly labeled as "zinc ion fluorescent probe compound+M", $F_0$ was the fluorescence of the blank solution, F was the fluorescence of the solution to be tested, the ultraviolet absorption at the wavelength of 254 nm was measured, and the ratio of F to $F_0$ was taken as intensity change).

Experimental Embodiment 2

In order to further verify the specificity of the zinc ion fluorescent probe compound to the zinc ion, a competitive experiment was conducted: adding the $Zn^{2+}$ solution (10 NM) into the probe solution formulated in step (1) together with a solution of any other one of the aforesaid metal ions of the same concentration; testing the effects of other competitive ions on the $Zn^{2+}$ selectivity of the zinc ion fluorescent probe compound respectively. The test results were shown in FIG. 3 (all test solution was uniformly labeled as "zinc ion fluorescent probe compound+M+Zn"). It could be seen that the detection of $Zn^{2+}$ by the zinc ion fluorescent probe compound had almost no change before and after the addition of other competitive ions, which indicated that the designed fluorescent probe compound of the zinc ion had a strong $Zn^{2+}$ selectivity and could meet the actual application requirements.

Experimental Embodiment 3

Figure 4:
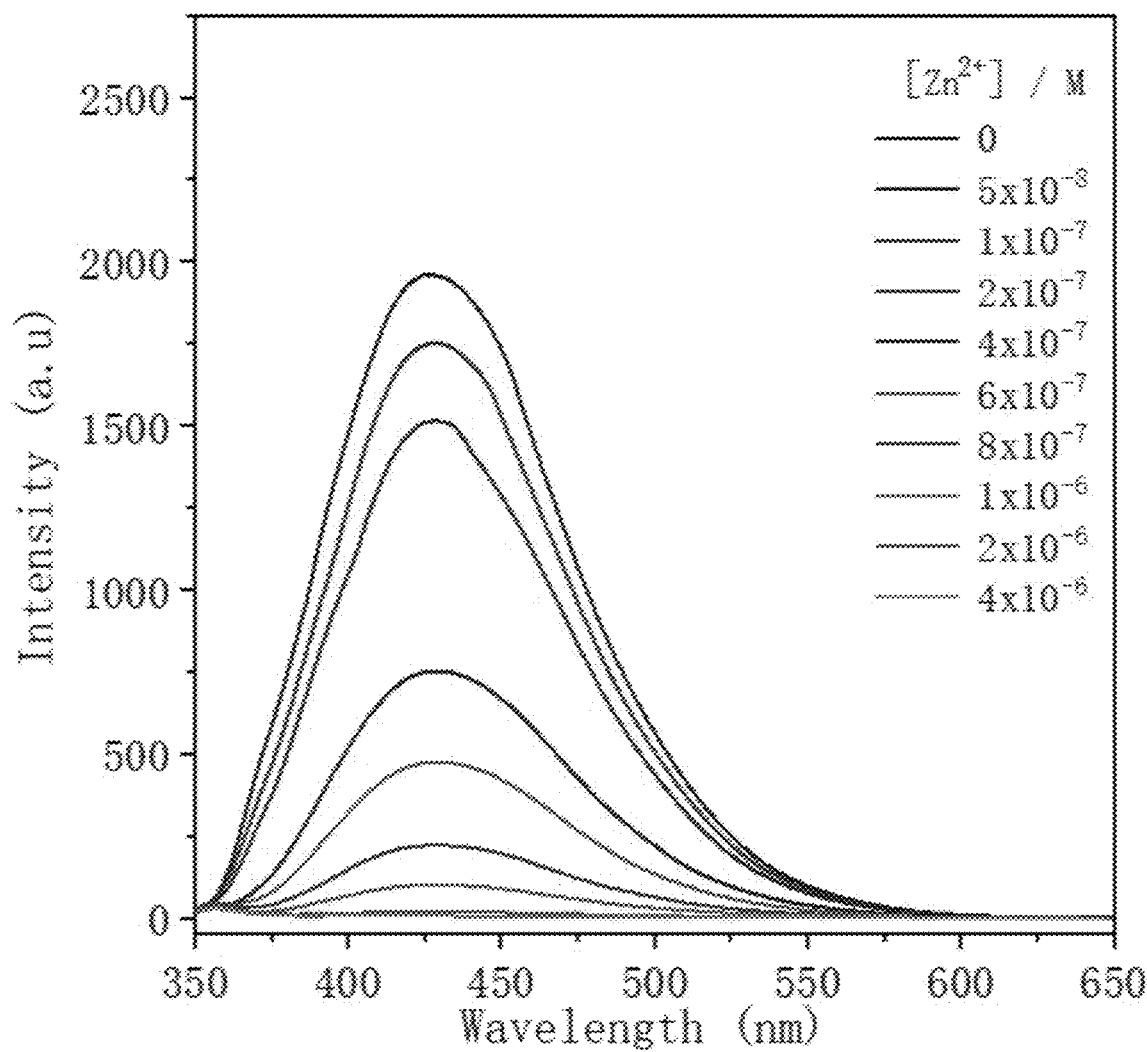
FIG. 4 is a graph of fluorescence performance test results of the fluorescent probe compound of the present disclosure under the condition of different $Zn^{2+}$ concentrations.

Different concentrations of $Zn^{2+}$ were added into the probe solution formulated in step (1) to test the fluorescence property of the probe solution, so as to determine the detection range and detection limit for $Zn^{2+}$ of the fluorescent probe compound. The test results were shown in FIG. 4, it can be seen that the concentrations of $Zn^{2+}$ were 0, 5×10-8 M, 1×10-7 M, 2×10-7 M, 4×10-7 M, 6×10-7 M, 8×10-7 M, 1×10-6 M, 2×10-6 M, 4×10-6 M sequentially, while the fluorescence intensities decreased from top to bottom accordingly, indicating that the fluorescence intensity of the fluorescent probe compound decreased gradually with the increase of $Zn^{2+}$ concentration. When the concentration of $Zn^{2+}$ reached 4×10-6 M, the fluorescence intensity of the compound had a dramatic decay. The detection range of the fluorescent probe compound for $Zn^{2+}$ was from 0.05 μM to 20 μM, and the detection limit was 5×10-8 M, which indicated that the compound had a relatively good $Zn^{2+}$ detection capability and a relatively high practical application value.

Experimental Embodiment 4

In order to further confirm the mechanism of interaction between the probe and the metal ion, a preliminary analysis was preformed using Job's plot. The specific operation method was as follows: ensuring the total concentration to be a constant (10 μM), testing the fluorescence emission spectrum at 426 nm at different molar ratios of the probe to the metal ion, and depicting a functional diagram of the variation of fluorescence intensity with the mole fraction of $Zn^{2+}$ according to the results. And the result was shown in FIG. 5.

Figure 5:
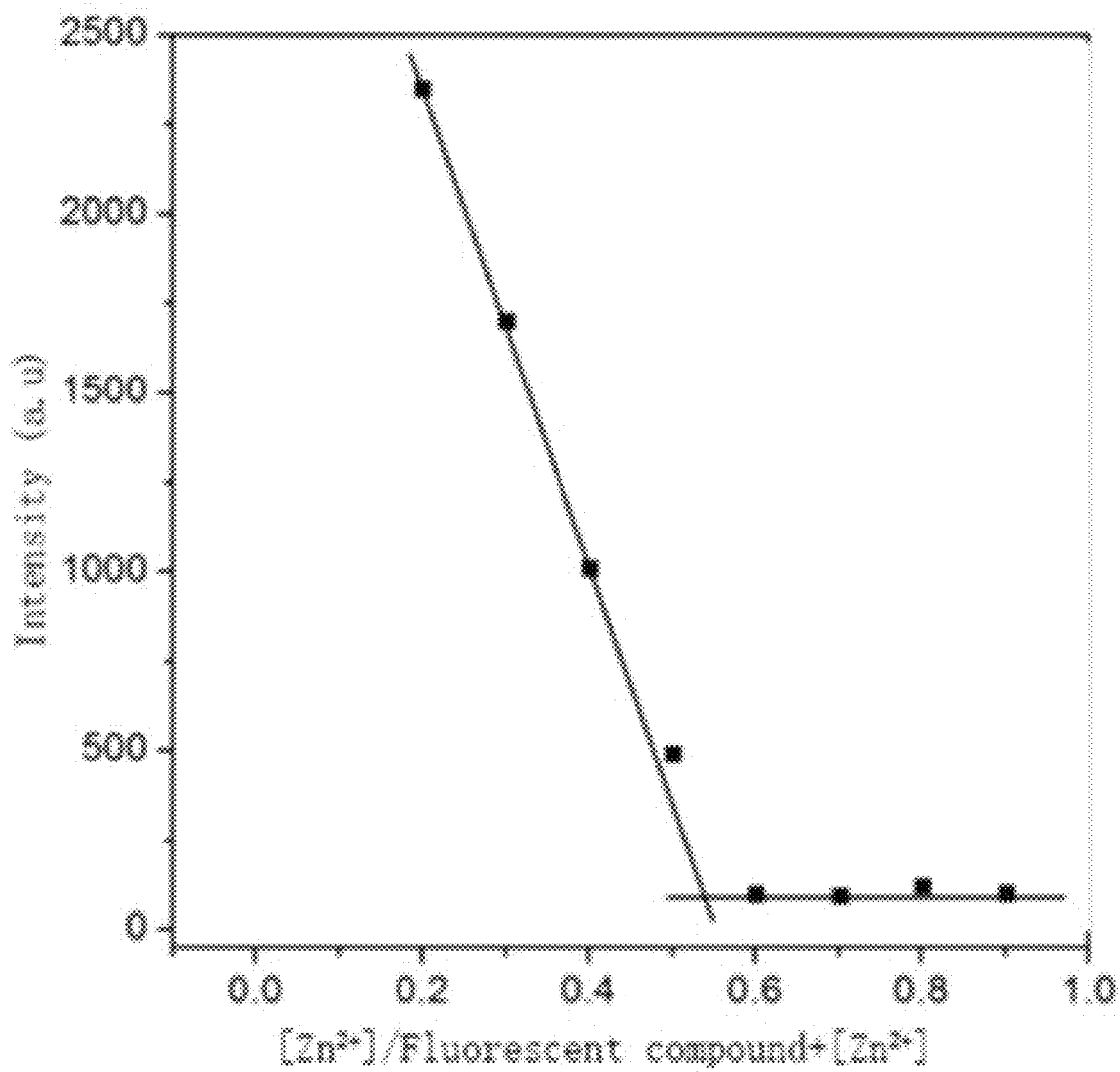
FIG. 5 is a functional relationship diagram of the variation of fluorescence intensity with the mole fraction of $Zn^{2+}$.
Figure 6:
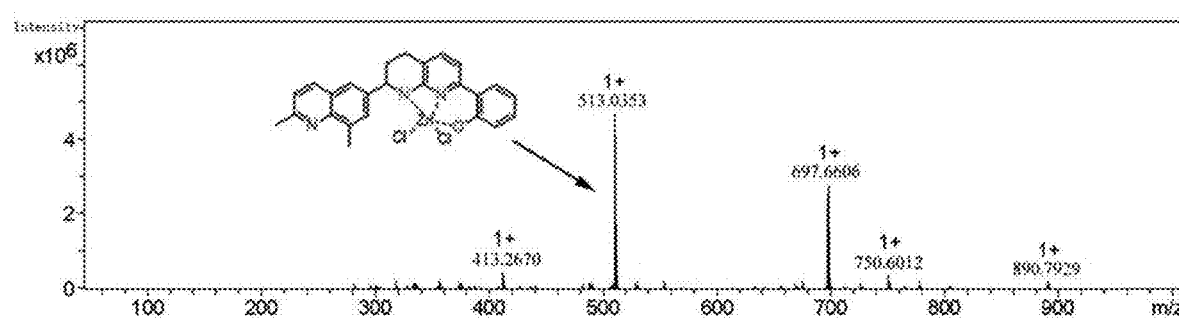
FIG. 6 is a results graph of high-resolution detection of the fluorescent probe compound of the present disclosure.

It could be seen from FIG. 5 that when the mole fraction of the zinc ion reached 0.51, one inflection point appeared, indicating that the zinc ion coordinated with the probe in a 1:1 relationship. Meanwhile, the aforesaid experimental results were further confirmed by the high-resolution detection data. As shown in FIG. 6, a major signal peak occurred at m/z 513.0353, this molecular weight was consistent with the molecular weight of C25H21Cl2N3OZn, of which the calculated value was 513.0347, which was within the error range. According to the aforesaid results, a possible coordination structure could be inferred (the structural formula shown in FIG. 6).

The above embodiments are preferred embodiments of the present disclosure, and the present disclosure is not limited thereto. Any other changes, modifications, substitutions, combinations, and simplifications made without departing from the spiritual essence and principle of the present disclosure shall be equivalent replacements, and all are included in the protection scope of the present disclosure.

What is claimed is:

1. A fluorescent probe compound, named as 2-(7-(2,8-dimethyl quinoline-6-yl)-5,6,7,8-tetrahydro-1,8-naphthyridin-2-yl) phenol, with the following structural formula:

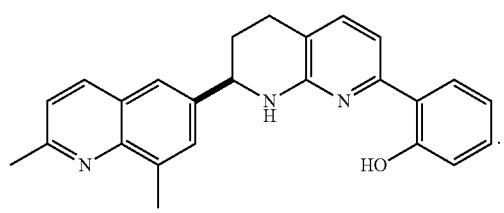

2. A preparation method of the fluorescent probe compound according to claim 1, comprising the following steps:

uniformly mixing 2,8-dimethyl tetrahydroquinoline, 2-(2-phenolyl)-1,8-naphthyridine, a metal catalyst, an acid and a solvent, reacting at 80-160° C. for 5-24 hours to obtain a crude product; and purifying the crude product to obtain the fluorescent probe compound.

3. The preparation method of the fluorescent probe compound according to claim 2, wherein a molar ratio of the 2,8-dimethyl tetrahydroquinoline to the 2-(2-phenolyl)-1,8-naphthyridine is 1:0.5-1.

4. The preparation method of the fluorescent probe compound according to claim 2, wherein the metal catalyst is selected from one or more of: copper acetate, copper trifluoromethylsulfonate, copper sulfate, copper chloride, cuprous chloride, ferric chloride, cobalt acetate, cobalt chloride and manganese acetate; and a mass of the metal catalyst is 1-5% of the mass of the 2,8-dimethyl tetrahydroquinoline.

5. The preparation method of the fluorescent probe compound according to claim 2, wherein the acid is selected from one or more of: formic acid, acetic acid, methylsulfonic acid, benzoic acid, p-toluenesulfonic acid, hydrochloric acid, trifluoromethylsulfonic acid, and trifluoroacetic acid; and a mass of the acid is 10-100% of the mass of the 2,8-dimethyl tetrahydroquinoline.

6. The preparation method of the fluorescent probe compound according to claim 2, wherein the solvent is selected from one or more of: ethanol, tert-pentanol, isopropanol, 1,4-dioxane, N,N-dimethyl formamide, dimethyl sulfoxide, toluene, p-xylene and water.

7. The preparation method of the fluorescent probe compound according to claim 2, wherein a volume molar ratio of the solvent to the 2,8-dimethyl tetrahydroquinoline is 0.5-3 mL:0.5 mmol.

8. The preparation method of the fluorescent probe compound according to claim 2, wherein the purifying is by column chromatography purification.

9. The preparation method of the fluorescent probe compound according to claim 8, wherein an eluent for the column chromatography purification is a mixed solution of petroleum ether:dichloromethane:ethyl acetate in a volume ratio of 0.5-50:0-20:1.

10. A zinc ion detection product comprising the fluorescent probe compound of claim 1.

* * * * *